(12) United States Patent
Winkler

(10) Patent No.: US 6,673,006 B2
(45) Date of Patent: Jan. 6, 2004

(54) TISSUE POSITIONING APPARATUS AND METHOD FOR PROTECTING TISSUE FROM RADIOTHERAPY

(75) Inventor: Rance A. Winkler, Atlanta, GA (US)

(73) Assignee: Proxima Therapeutics, Inc., Alpharetta, GA (US)

( * ) Notice: Subject to any disclaimer, the term of this patent is extended or adjusted under 35 U.S.C. 154(b) by 132 days.

(21) Appl. No.: 09/882,506

(22) Filed: Jun. 15, 2001

(65) Prior Publication Data

US 2002/0193653 A1 Dec. 19, 2002

(51) Int. Cl.[7] ................................................ A61N 5/00
(52) U.S. Cl. ........................ 600/1; 600/3; 600/7; 600/8
(58) Field of Search ........................................ 600/1–8

(56) References Cited

U.S. PATENT DOCUMENTS

| | | | |
|---|---|---|---|
| 3,872,856 A | 3/1975 | Clayton | 128/1.2 |
| 4,665,906 A | 5/1987 | Jervis | 128/92 |
| 4,706,652 A | 11/1987 | Horowitz | 128/1.2 |
| 4,754,745 A | 7/1988 | Horowitz | 128/1.2 |
| 5,411,466 A * | 5/1995 | Hess | 600/3 |
| 5,422,926 A | 6/1995 | Smith et al. | 378/121 |
| 5,429,582 A | 7/1995 | Williams | 600/2 |
| 5,484,384 A * | 1/1996 | Fearnot | 600/3 |
| 5,562,594 A | 10/1996 | Weeks | 600/3 |
| 5,724,400 A | 3/1998 | Swerdloff et al. | 378/65 |
| 5,800,333 A | 9/1998 | Liprie | 600/3 |
| 5,803,895 A | 9/1998 | Kronholz et al. | 600/3 |
| 5,851,182 A | 12/1998 | Sahadevan | 600/407 |
| 5,863,284 A | 1/1999 | Klein | 600/3 |
| 5,913,813 A * | 6/1999 | Williams et al. | 600/3 |
| 6,036,631 A | 3/2000 | McGrath et al. | 600/3 |
| 6,066,856 A | 5/2000 | Fishman | 250/519.1 |
| 6,149,574 A * | 11/2000 | Trauthen et al. | 600/3 |
| 6,159,207 A | 12/2000 | Yoon | 606/41 |

FOREIGN PATENT DOCUMENTS

| | | |
|---|---|---|
| EP | 0867200 | 9/1998 |
| WO | 9719723 | 6/1997 |
| WO | 9911325 | 3/1999 |
| WO | 9933515 | 7/1999 |
| WO | 9942163 | 8/1999 |
| WO | 0074573 | 12/2000 |

OTHER PUBLICATIONS

Ravinder, Nath, Ph.D. et al., Development of an[241] Am Applicator For Intracavitary Irradiation of Gynecologic Cancers, I.J. Radiation Oncology, Biology, Physics, May 1988, vol. 14, No. 5.

* cited by examiner

Primary Examiner—John Rivell
Assistant Examiner—Amanda Flynn
(74) Attorney, Agent, or Firm—Thomas Engellenner; Nutter, McClennen & Fish LLP

(57) ABSTRACT

A spacing apparatus for use with radiation therapy devices, and in particular, for use with a brachytherapy device. The spacing apparatus is useful in that the instrument is effective to limit the amount of radiation that comes into contact with the sensitive tissue proximate to the extraction site, and thereby protect sensitive tissue from overheating or hotspots, and/or protect against radiation exposure outside of the patient's body which may affect healthcare providers or others who might come close to the patient. In particular, the spacing apparatus is effective to control the proximity of a brachytherapy device to the outer surface of the sensitive tissue proximate to a surgical extraction site.

19 Claims, 8 Drawing Sheets

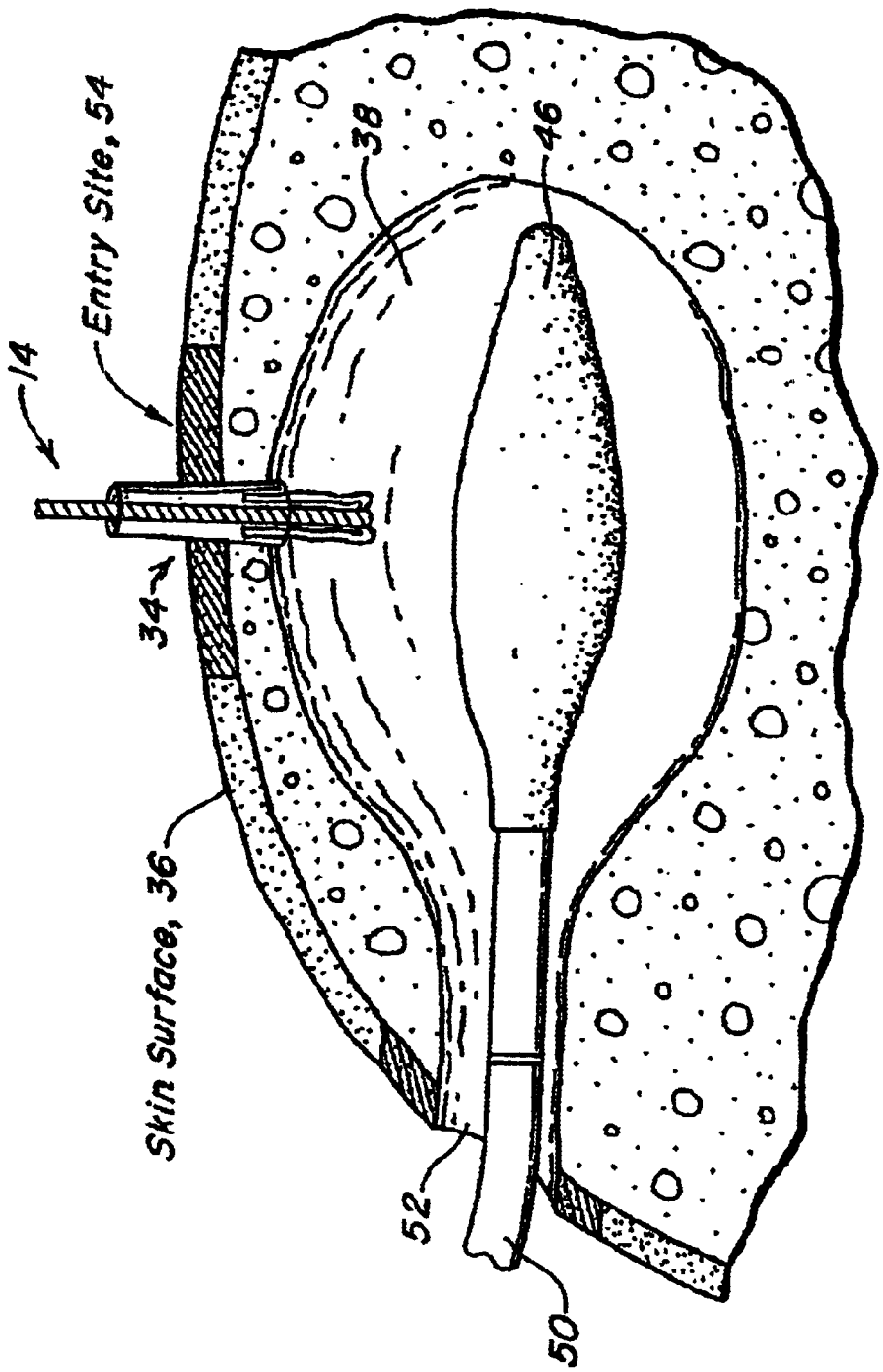

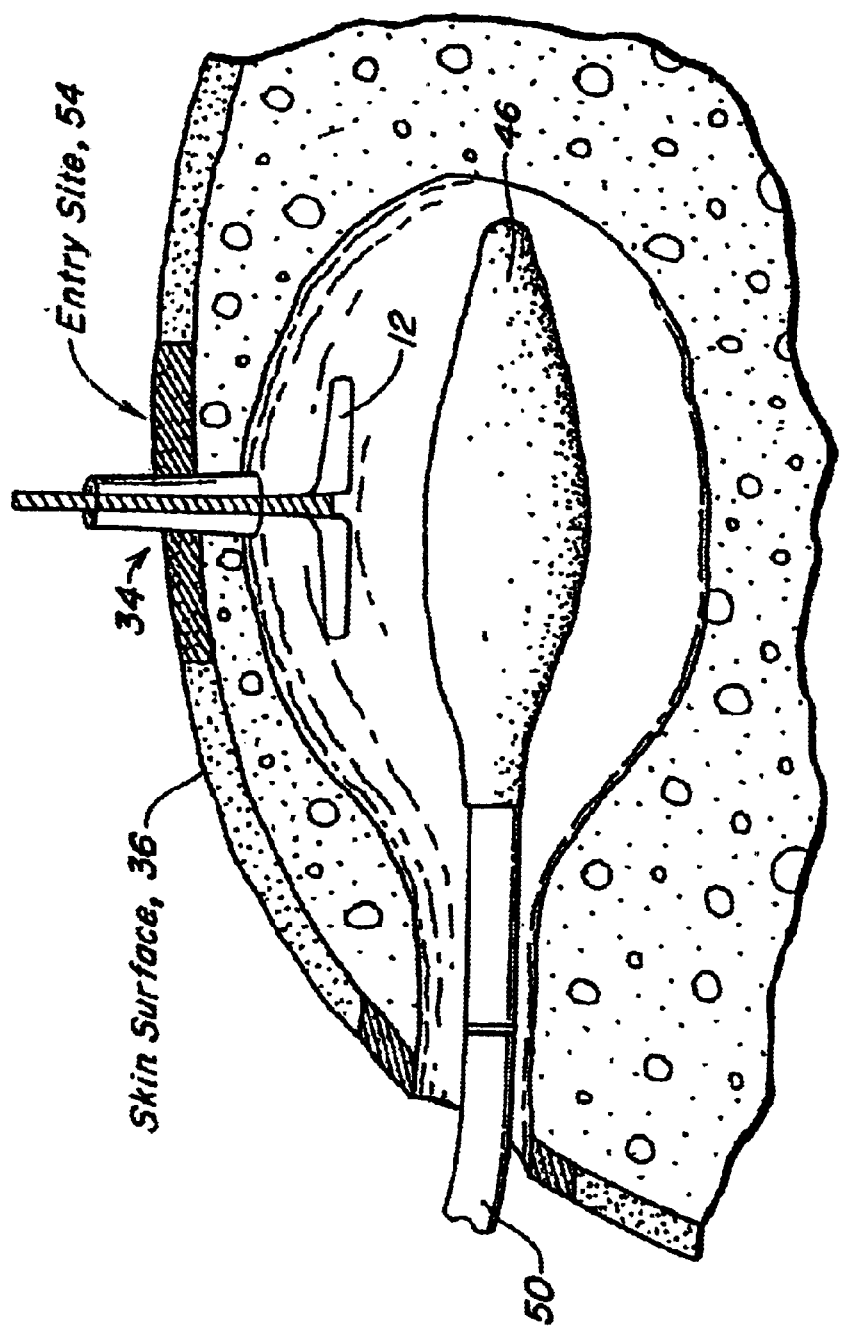

TISSUE POSITIONING APPARATUS AND METHOD FOR PROTECTING TISSUE FROM RADIOTHERAPY

FIELD OF THE INVENTION

The present invention relates to methods and apparatuses for use in treating proliferative tissue disorders, and more particularly to methods and apparatus for controlling the positioning of a radiation therapy apparatus with respect to the sensitive tissue.

BACKGROUND OF THE INVENTION

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it. Radiation therapy can be administered through one of several methods, or a combination of methods, including external-beam radiation, stereotactic radiosurgery, and permanent or temporary interstitial brachytherapy. The term "brachytherapy," as used herein, refers to radiation therapy delivered by a spatially confined radioactive material inserted into the body at or near a tumor or other proliferative tissue disease site. Owing to the proximity of the radiation source, brachytherapy offers the advantage of delivering a more localized dose to the target tissue region.

Brachytherapy can be performed by implanting radiation sources directly into the tissue to be treated. Interstitial brachytherapy is traditionally carried out using radioactive seeds such as $^{125}$I seeds. These seeds, however, produce inhomogeneous dose distributions. In order to achieve a minimum prescribed dosage throughout a target region of tissue, high activity seeds must be used, resulting in very high doses being delivered in some regions in proximity to the seed or seeds which can cause radionecrosis in healthy tissue. Interstitial brachytherapy is useful for treating malignant brain and breast tumors, among others.

The absorbed dose rate in a target tissue exterior to a radioactive source is inversely proportional to the square of the distance between the radiation source and the target point. As a result, where the radioactive source has sufficient activity to deliver a prescribed dose, say 2 centimeters into the target tissue, the tissue directly adjacent the wall of the distensible reservoir, where the distance to the radioactive source is very small, may still be overly "hot" to the point where sensitive but otherwise healthy tissue necrosis may result.

In general, the amount of radiation desired by the physician is a certain minimum amount that is delivered to a region up to about two centimeters away from the wall of the excised tumor. It is desirable to keep the radiation that is delivered to the tissue in the target treatment region within a narrow absorbed dose range to prevent over-exposure to tissue at or near the radiation source, while still delivering the minimum prescribed dose at the maximum prescribed distance from the radiation source. It is also desirable, at least in some applications, to provide these advantages while tailoring the radiation dosage to avoid fully dosing sensitive tissue or to reduce the amount of radiation that escapes the patient's body.

Thus, there is a need for an instrument which can be used to deliver radiation from a radioactive source to target tissue within the human body with a desired intensity and at a predetermined distance from the radiation source without over-exposure of sensitive body tissues, such as skin or organ tissue for example, disposed proximate to the radiation.

SUMMARY OF THE INVENTION

The present invention provides a positioning or spacing apparatus and methods of use for positioning a radiotherapy device, such as a brachytherapy device, at a distance apart from the outer surface of the tissue proximate to a surgical extraction site. The spacing apparatus is useful in that the instrument is effective to limit the amount of radiation that comes into contact with the adjacent tissue, and thereby protect sensitive tissue from overheating or hotspots, and/or protect against radiation exposure outside of the patient's body which may affect healthcare providers or others who might come close to the patient.

In general, the spacing apparatus according to the present invention includes a spacing element that can have any shape and size, but is preferably adapted to provide a sufficient amount of space, hereinafter referred to as the desired spacing, between the brachytherapy device and the outer surface of the tissue adjacent the extraction site. The desired spacing is preferably adapted to prevent damage to healthy tissue cells, while allowing cancerous cells to be destroyed. The spacing apparatus can be mated to or disposed in conjunction with a brachytherapy device, or alternatively, can be introduced via a separate insertion device for use with any brachytherapy device. The size and shape of the spacing element can vary, and the spacing element can be movable between an open position and a closed position.

In one embodiment, the spacing element is formed from an expandable balloon member. In the closed, deflated position, the balloon member is disposed or folded around an insertion member to allow the insertion member to be inserted through an opening, e.g. an introducer sheath, into a surgical extraction site. Once inserted, the balloon member can be inflated to the open position to provide a predetermine amount of space between a brachytherapy device and the tissue surrounding the extraction site. The necessary spacing is preferably equal to the height of the spacing element which is predeterminable—that is, the height can be fixed and predetermined, or the spacing element can be of a variable height that is selectable in use. The balloon member can have a preformed shape such that, when inflated, the balloon member is effective to provide the necessary spacing between the brachytherapy device and the adjacent tissue.

In another embodiment, the spacing element is formed from a shape memory material and is biased to the open position, in which the spacing element has a three-dimensional shape. The three-dimensional shape can be, for example, a disk-shaped member which folds around the insertion member. In another embodiment, the spacing element can have a substantially folded V-shape in the closed position, and can be substantially L-shaped in the open position. In use, the spacing element is biased into the closed position by an introducer sheath during insertion into the surgical extraction site and, once fully inserted, is free to move to the open position to provide the necessary amount of spacing between the brachytherapy device and the sensitive tissue proximate to the extraction site.

In other aspects of the invention, a brachytherapy device is provided having an insertion member with proximal and distal ends, a first expandable balloon member disposed on the distal end of the insertion member, and a spacing element disposed on the distal end of the insertion member proximal to the first expandable balloon member. The expandable balloon member is effective to receive a radiation source for treating target tissue surrounding a surgical extraction site, and the spacing element is effective to position the expandable balloon member at a distance apart from the tissue surrounding the extraction site. The spacing element of the brachytherapy device can be movable between an open position and a closed position, and can be formed from an expandable balloon member, a shape memory material, or other similar structures. In a preferred embodiment, the first expandable balloon member, upon inflation, is effective to move the spacing element from a closed position to an open position.

In another embodiment of the present invention, a brachytherapy system is provided having a brachytherapy device for treating target tissue surrounding a surgical extraction site, and a spacing apparatus for positioning the brachytherapy device at a distance apart from sensitive tissue proximate to the surgical extraction site. The spacing apparatus can include an insertion member having proximal and distal ends, and a spacing element disposed on the distal end of the insertion member.

The present invention also provides methods for positioning a brachytherapy device at a distance apart from tissue surrounding a surgical extraction site. In one embodiment, the method can include the steps of introducing a spacing apparatus having a predeterminable height into a surgical extraction site, introducing a brachytherapy device for treating target tissue into the surgical extraction site, and positioning the spacing apparatus with respect to the brachytherapy device so as to position the device at a distance equal to the height of the spacing element apart from the tissue surrounding the surgical extraction site. The spacing apparatus and the brachytherapy device can be introduced into the surgical extraction site through separate entrances ports, or though the same entrance port. Moreover, the spacing apparatus can be mated to or formed integrally with the brachytherapy device.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which:

FIG. 5B illustrates the spacing apparatus shown in FIG. 5A partially inserted into the surgical extraction site;

FIG. 5C illustrates the spacing apparatus of FIG. 5A fully inserted into the surgical extraction site.

DESCRIPTION OF THE INVENTION

Figure 1A:
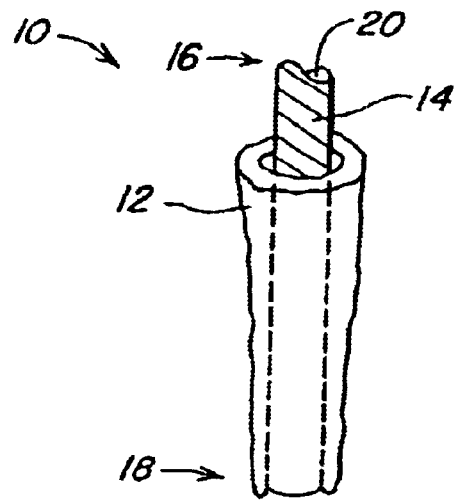
FIG. 1A is perspective view of a spacing apparatus according to one embodiment of the present invention.

The present invention relates to methods and apparatuses for controlling the proximity of a radiotherapy device to the outer surface of the sensitive tissue proximate to a surgical extraction site. Ideally, radiation therapy should make use of the inherent difference in radiosensitivity between tumor cells and the adjacent normal tissues cells to destroy cancerous tissue while causing minimal disruption to surrounding normal tissues. At high doses of radiation, the percentage of exposed cells that survive treatment decreases with first-order kinetics in proportion to increasing radiation dose. With increasing cell death comes increasing risk of necrosis or tissue death in healthy tissue that is treated with a high dose of radiation.

Accordingly, the present invention provides a positioning or spacing apparatus, and methods of use for positioning a radiotherapy device, such as a brachytherapy device, at a distance apart from the outer surface of the tissue proximate to a surgical extraction site. The instrument is effective to limit the amount of radiation that comes into contact with the adjacent tissue, and thereby protect sensitive tissue from overheating or hotspots, and/or protect against radiation exposure outside of the patient's body which may affect healthcare providers or others who might come close to the patient.

The term "brachytherapy device" as used herein is intended to refer to radiation therapy delivered into the body at or near a tumor or other proliferative tissue disease site. However, a person having ordinary skill in the art will appreciate that the spacing apparatus disclosed herein can be used to position any type of radiation device or other medical device at a distance apart from tissue surrounding a surgical site.

By way of non-limiting example, a suitable brachytherapy device for use with the spacing apparatus of the present invention is disclosed in U.S. patent No. 6,413,204, filed Apr. 15, 1999, and entitled "Interstitial Brachytherapy Apparatus and Method for the Treatment of Proliferative Tissue Diseases," which is hereby incorporated by reference herein. In addition, this application provides detailed information on the effects of spacing on radiation dosing. While the aforementioned application provides examples of a brachytherapy device useful with the invention described herein having an outer expandable surface (such as an inflatable balloon for example) with a radiation source disposable inside the surface, a person of ordinary skill in the art will understand that other brachytherapy device configurations may be used within the spirit of the present invention.

In general, the spacing apparatus according to the present invention includes a spacing element that can have any shape and size, but is preferably adapted to provide a sufficient amount of space, hereinafter referred to as the desired spacing, between the brachytherapy device and the outer surface of the tissue adjacent the extraction site. The desired spacing is preferably adapted to prevent damage to healthy tissue cells, while allowing cancerous tissue to be destroyed. The spacing apparatus can be mated to or disposed in conjunction with a brachytherapy device, or alternatively, can be introduced via a separate insertion device for use with any brachytherapy device. In use, the spacing element can be inserted through an introducer sheath and, once inserted, opens or extends outward to provide distance between the brachytherapy device and the adjacent tissue.

Figure 1B:
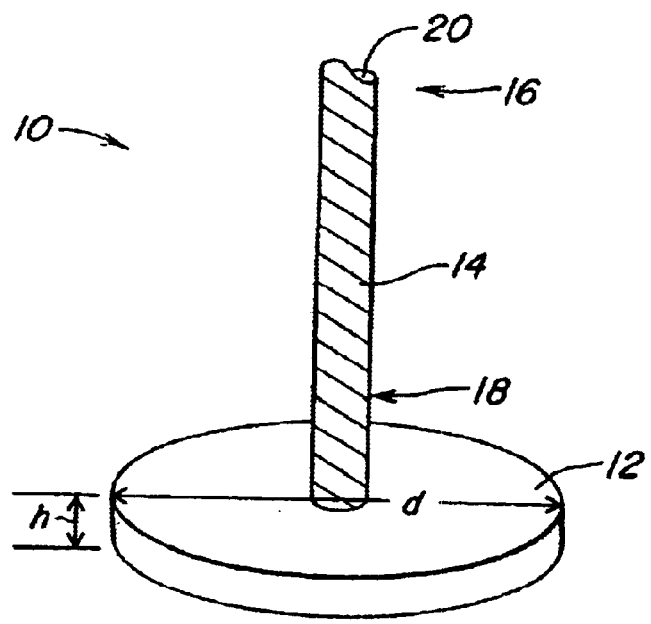
FIG. 1B is a perspective view of the spacing apparatus of FIG. 1A in an open, extended position.

FIGS. 1A and 1B illustrate one embodiment of a spacing apparatus 10 according to the present invention for use with a separate brachytherapy device. In general, the spacing apparatus 10 includes a spacing element 12 and an elongate insertion member 14 having a proximal end 16 and a distal end 18. The elongate member 14 can optionally include an inner lumen 20, and can be a catheter, introducer sheath, or similar device. The spacing element 12 can be disposed within the inner lumen 20, disposed on or mated to a portion of the distal end 18 of the elongate member 14, or alternatively, can be formed integrally with the elongate member 14.

As shown in FIG. 1B, the spacing element 12 is substantially disk-shaped and includes a height h. The height h defines the desired spacing between the tissue adjacent to the extraction site and the brachytherapy device disposed within the extraction site. The height h can be determined based on the amount of radiation being provided, and the distance between the radiation source and the tissue surrounding the extraction site. While the spacing apparatus can have any height h, preferably, the height is between about 1 and 5 millimeters, and more preferably is about 3 millimeters.

FIG. 1B also illustrates the spacing element 12 having a diameter d, which extends in a direction substantially perpendicular to the elongate member 14. The diameter d of the spacing element can vary, but is preferably determined based upon the intended use of the spacing element. For example, the spacing element can be adapted to protect or shield a particular area of tissue, and therefore the diameter can be determined based upon the amount of surface area to be protected and the configuration of the brachytherapy device. Preferably, the diameter d is between about 20 and 60 millimeters, and more preferably is about 40 millimeters.

While FIG. 1B illustrates a substantially disk-shaped spacing element 12, a person having ordinary skill in the art will appreciate that the spacing element 12 can have any shape, such as square, oval, rectangular, etc., and can be flat or three-dimensional. In addition, diameter dimension d of the spacing element could represent any major dimension of a non-disk-shaped spacing element other than its height.

In use, the spacing element 12 can be movable between a closed position, shown in FIG. 1A, wherein the spacing element 12 is substantially disposed around the elongate member 14, and an open or deployed position shown in FIG. 1B, wherein the spacing element 12 is extended outward from the elongate member 14 in a direction substantially perpendicular to the elongate member 14. As shown in FIG. 1A, the spacing element 12 is disposed upward toward the proximal end 16 of the elongate member 14 to prevent the spacing element 12 from opening during insertion through an introducer sheath (not shown). This can be accomplished by a variety of techniques, such as, for example, pleats formed in the spacing element 12, twisting or rolling of the spacing element 12 around the elongate member 14, or other similar techniques. The spacing element 12 can also be formed from an elastic material which allows the spacing element 12 to wrap around the elongate member 14 in the closed position, and stretch outward from the elongate member 14 in the open position.

A person having ordinary skill in the art will readily appreciate that the spacing element 12 can be disposed in a distal facing direction in the closed position, or can be disposed around or within the elongate member 14 in any manner that allows the spacing apparatus 10 to be inserted through an introducer sheath and then extended into the open position.

Figure 2A:
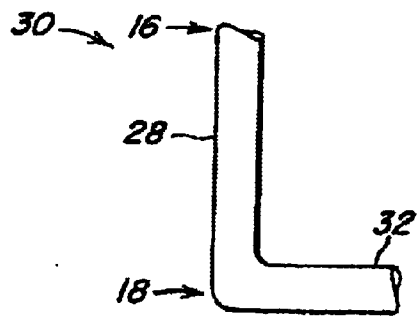
FIG. 2A is a perspective view of an additional embodiment of a spacing apparatus of the present invention formed from a shape memory material.
Figure 2B:
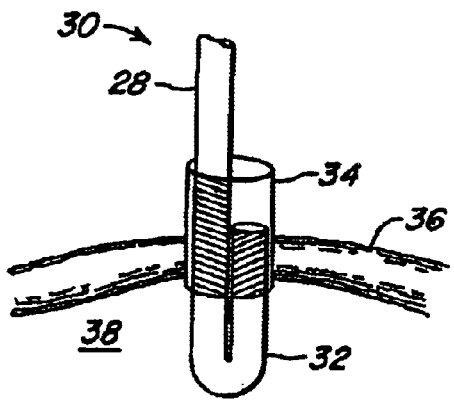
FIG. 2B is a perspective view of the spacing apparatus of FIG. 3A partially inserted into an introducer sheath.
Figure 2C:
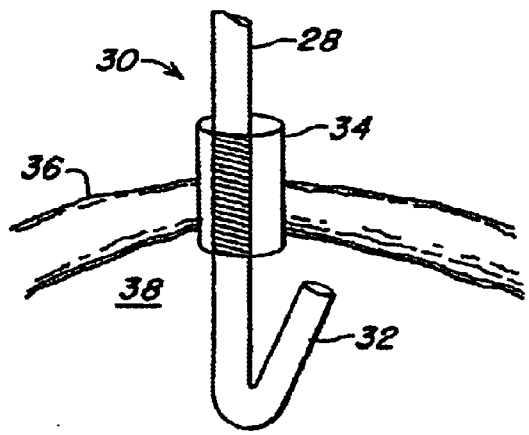
FIG. 2C is a perspective view of the spacing apparatus of FIG. 3A fully inserted through an introducer sheath and into an extraction site.
Figure 2D:
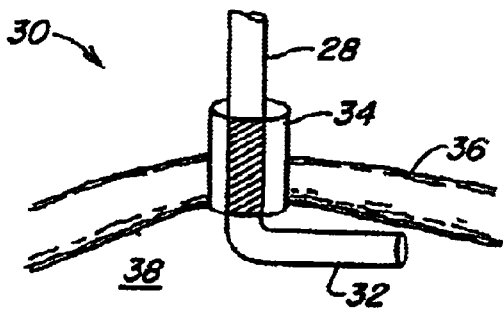
FIG. 2D is a perspective view of the spacing apparatus of FIG. 3A positioned to space a brachytherapy device a distance apart from sensitive tissue proximate to the extraction site.

In an alternative embodiment, the spacing element 12 can be formed integrally with the elongate member 14. By way of non-limiting example, FIG. 2A illustrates a spacing apparatus 30 having a spacing element 32 integrally formed on the distal end 18 of an elongate member 28, and being formed from a shape memory material. The shape memory material can be a metal shape memory material such as, for example, those disclosed in U.S. Pat. No. 4,665,906 (which is hereby incorporated by reference), NITINOL® (a commercially available nickel titanium alloy shape memory material), or a composite polymer material having shape memory qualities. The spacing element 32 is shown having an L-shape such that the spacing element 32 extends in a direction substantially perpendicular to the elongate member 28 in its pre-formed position. In use, the introducer sheath 34 holds the spacing element 32 adjacent the elongate member 28 during insertion of the apparatus 30 through the introducer sheath 34, as shown in FIG. 2B. Alternatively, the spacing element 32 can be inserted through an introducer sheath in a substantially straight, fully extended position (not shown). Once the spacing apparatus 30 is fully inserted through the introducer sheath, shown in FIG. 2C, the spacing element 32 resumes (due either to a release of steric constraints or a temperature increase from being placed inside the body) its preformed shape. The spacing apparatus 30 can then be retracted to position the spacing element 32 adjacent the tissue 36 proximate to the extraction site 38. While an L-shaped spacing element 32 is illustrated in FIG. 2B, a person of ordinary skill in the art will recognize that any appropriate shape could be used, including a circularly shaped spacing element formable in a plane that is perpendicular to a longitudinal axis of elongate member 28.

Movement of the spacing element 12, 32 according to the present invention between the open and closed positions can be accomplished by a variety of techniques. For example, the spacing apparatus 10, 30 can optionally include an actuating member (not shown), such as a wire, pulley assembly, lever, or similar device, effective to move the spacing element 12, 32 to a position adjacent to the elongate member 20, 28 to allow for insertion of the apparatus 10, 30 through an introducer sheath, and/or to return the spacing element 12, 32 to the open position once inserted. A person having ordinary skill in the art will readily appreciate that a variety of different actuating members can be used to position the spacing element 12, 32 within the extraction site 38.

Figure 3A:
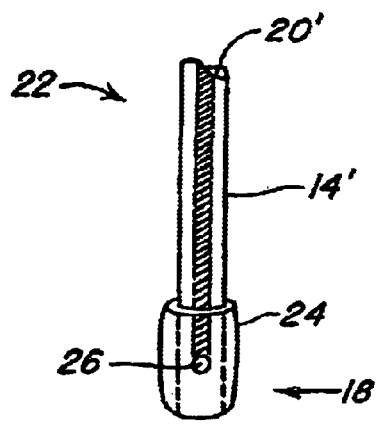
FIG. 3A is a perspective view of another embodiment of a spacing apparatus having an inflatable balloon member according to the present invention.
Figure 3B:
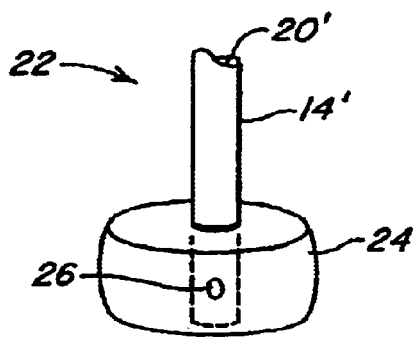
FIG. 3B is a perspective view of the spacing apparatus of FIG. 2A illustrating the balloon member in a partially inflated position.
Figure 3C:
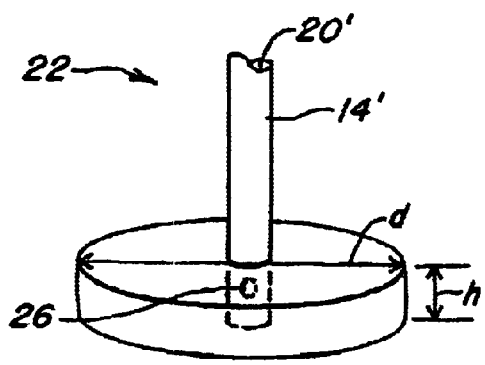
FIG. 3C is a perspective view of the spacing apparatus of FIG. 2A illustrating the balloon member in a fully inflated position.

FIGS. 3A–3C illustrate another embodiment of a spacing apparatus 22 according to the present invention having a spacing element 24 formed from an inflatable balloon member, and an elongate member 14' similar in purpose and construction to elongate member 14 discussed with respect to FIGS. 1A–1B. The elongate member 14' includes an inner lumen 20' defining a pathway, and a port 26 in communication with the inner lumen 20' for providing air or liquid to inflate the spacing element 24. The elongate member 14' can optionally include an open distal end in communication with a second inner lumen (not shown) for receiving a brachytherapy device.

The spacing element 24 is primarily sealed around the port 26 on the distal end 18 of the elongate member 14', and can include a predetermined shape in its expanded form, shown in FIG. 3C, such that, when inflated, the balloon has a height h which is adapted to provide the desired spacing between the brachytherapy device and the tissue adjacent the extraction site. A person having ordinary skill in the art will readily appreciate that the spacing element 24 can have any shape, height h, as well as any diameter d, so long as the spacing element 24 is effective to provide the desired spacing between a brachytherapy device and the tissue adjacent the extraction site. The height h and the diameter d of spacing element 24 can be the same or similar to the height h and the diameter d of spacing element 12 described with respect to FIG. 1B. In addition, the height h of spacing element 24 can be selectable during treatment by inflating the balloon to a desired level so as to have the selected height.

Figure 4A:
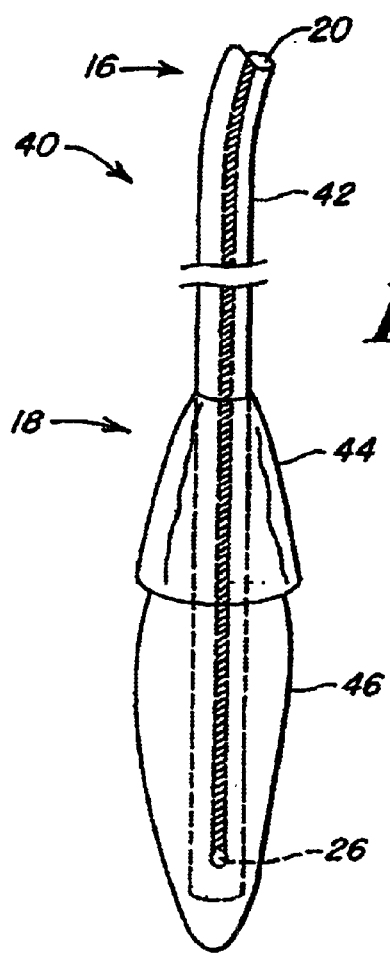
FIG. 4A is a perspective view of yet another embodiment of a spacing apparatus of the present invention having a spacing element disposed on a brachytherapy device.
Figure 4B:
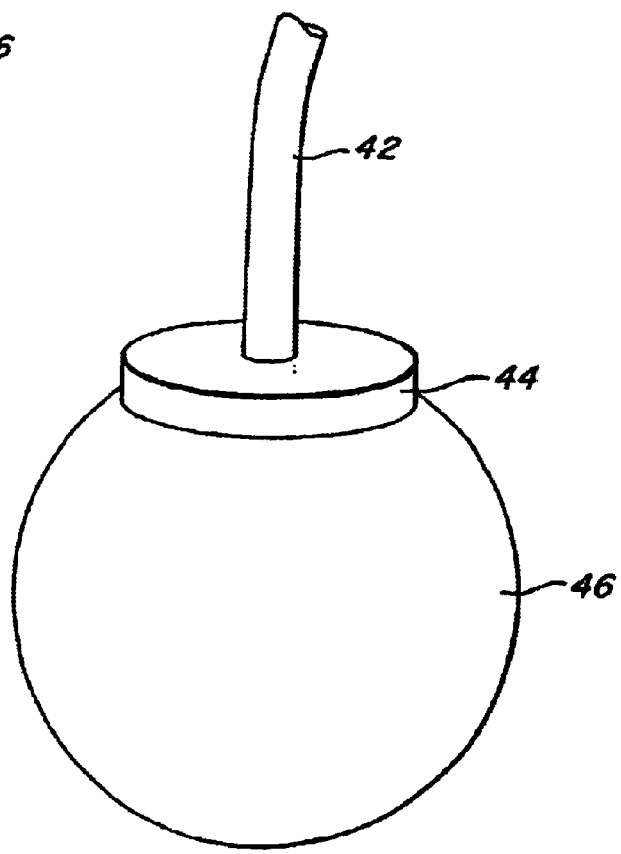
FIG. 4B illustrates the spacing apparatus of FIG. 4A in an open, extended position.

In another embodiment of the present invention, as shown in FIGS. 4A and 4B, the spacing apparatus can be mated to or disposed on a brachytherapy device. FIG. 4A illustrates a brachytherapy device 40 having an elongate member 42, a spacing element 44, and an expandable balloon member 46 for receiving a radiation source. The expandable balloon member 46 and the spacing element 44 are disposed on a distal end 18 of the elongate member 42, the spacing element 44 being disposed proximally to the balloon member 46. The elongate member 42 includes at least one inner lumen 20 in communication with a port 26 formed in the distal end 18 of the elongate member 42. The inner lumen 20 is effective to carry a radioactive source and/or an inflation source to the expandable balloon member 46 for inflating the balloon 46, and/or applying radiation to the extraction site.

The spacing element 44 is similar in purpose and construction to spacing elements 12 and 24 described with respect to FIGS. 1A–1B, and 3A–3C. Thus, the spacing element 44 can have any shape and size, and can be formed integrally with the elongate member 42, can be an expandable balloon member disposed on, around, or within the elongate member 42, or can be any other type of structure effective for positioning a brachytherapy device at a distance apart from the surface of sensitive tissue proximate to the extraction site. The spacing element 44 is movable between a closed position shown in FIG. 4A, and an open position shown in FIG. 4B. Movement can be accomplished by an actuating member (not shown), or alternatively, the spacing element 44 can be formed from a shape memory material to allow the spacing element 44 to be positioned properly once disposed within the extraction site. In a preferred embodiment, the expandable balloon member 46 is effective to move the spacing element 44 to the open position, shown in FIG. 4B, upon expanding the balloon member 46.

The spacing apparatus according to the present invention can be formed from a variety of materials. Suitable materials include plastic, metal, composite materials, and the like. The spacing apparatus can optionally be from radiopaque materials, or can include a radiopaque coating on all or a portion of the spacing element. Suitable radiopaque materials include, for example, barium, tungsten, bismuth, tantalum and tin.

The spacing apparatus of the invention can be used in the treatment of a variety of malignant tumors, and is especially useful in the treatment of brain and breast tumors. Surgery and radiation therapy are the standard treatments for malignant tumors. The goal of surgery is to remove as much of the tumor as possible without damaging vital tissue. The ability to remove the entire malignant tumor is limited by its tendency to infiltrate adjacent normal tissue. Partial removal reduces the amount of tumor to be treated by radiation therapy and, under some circumstances, such as with brain tumors, helps to relieve symptoms by reducing pressure on the brain.

A common method for treating these and other malignancies begins by surgical resection of a tumor site to remove at least a portion of the cancerous tumor and create a resection cavity. Following tumor resection, but prior to closing the surgical site, the surgeon intra-operatively places an interstitial brachytherapy catheter apparatus into the tumor resection cavity. The interstitial brachytherapy catheter can be loaded with a radiation source either during surgery or following recovery from surgery as medically appropriate. The radioactive source dwells in the catheter until the prescribed dose of radiotherapy is delivered, or the radiation source can be inserted for prescribed amounts of time on a daily or other scheduled basis until the prescribed dosage has been achieved. The radiation source is then retrieved and the catheter is removed. The radiation treatment may end upon removal of the brachytherapy apparatus, or the brachytherapy may be supplemented by further doses of radiation supplied externally.

The spacing apparatus described herein is useful for positioning the brachytherapy apparatus at a distance apart from the sensitive tissue proximate to the extraction site. The spacing apparatus can be inserted through the same surgical entry site as the brachytherapy apparatus, or alternatively can be inserted through a separate entry site. A person having ordinary skill in the art will appreciate that a variety of different methods can be used for positioning a brachytherapy device at a distance apart from the outer surface of the tissue adjacent the extraction site.

By way of non-limiting example, FIGS. 5A–5D illustrate a spacing apparatus 10, as described with respect to FIGS. 1A–1B, in use with a brachytherapy device 50 to treat a breast cancer. As an initial step, surgical access to the site of the cancerous tumor is created and the bulk of the tumor is surgically resected. Spacer 10 and brachytherapy device 50 can then be deployed to treat remaining cancer cells while protecting sensitive tissue such as skin 36.

Brachytherapy device 50, comprising generally an inflatable balloon 46 for housing a radiation source disposed on the distal end of catheter 56, is inserted (FIG. 5A) into a resection cavity 38 through surgical entry site 52, which may be the surgical approach through which the tumor was resected or an opening created specifically for deployment of brachytherapy device 50. Spacing apparatus 10 can be inserted (FIG. 5B) into resection cavity 38 through a separate entry site 54 through introducer sheath 34. A person of ordinary skill in the art will recognize that spacer 10 and brachytherapy device 50 can be inserted into resection cavity 38 in any order, and that spacer 10 can be inserted through either separate entry site 54 or through surgical entry site 52 depending on the configuration of spacer 10. For example, spacer 44 of FIGS. 4A and 4B must be inserted through the same entry site as brachytherapy device 46 as spacer 44 is connected to the brachytherapy device. On the other hand, spacing element 30 of FIGS. 2A–2D, because of its configuration, could be inserted through either surgical entry site 52 or separate entry site 54. In the example illustrated in FIGS. 5A–5D, a separate entry site 54 is used.

Figure 5A:
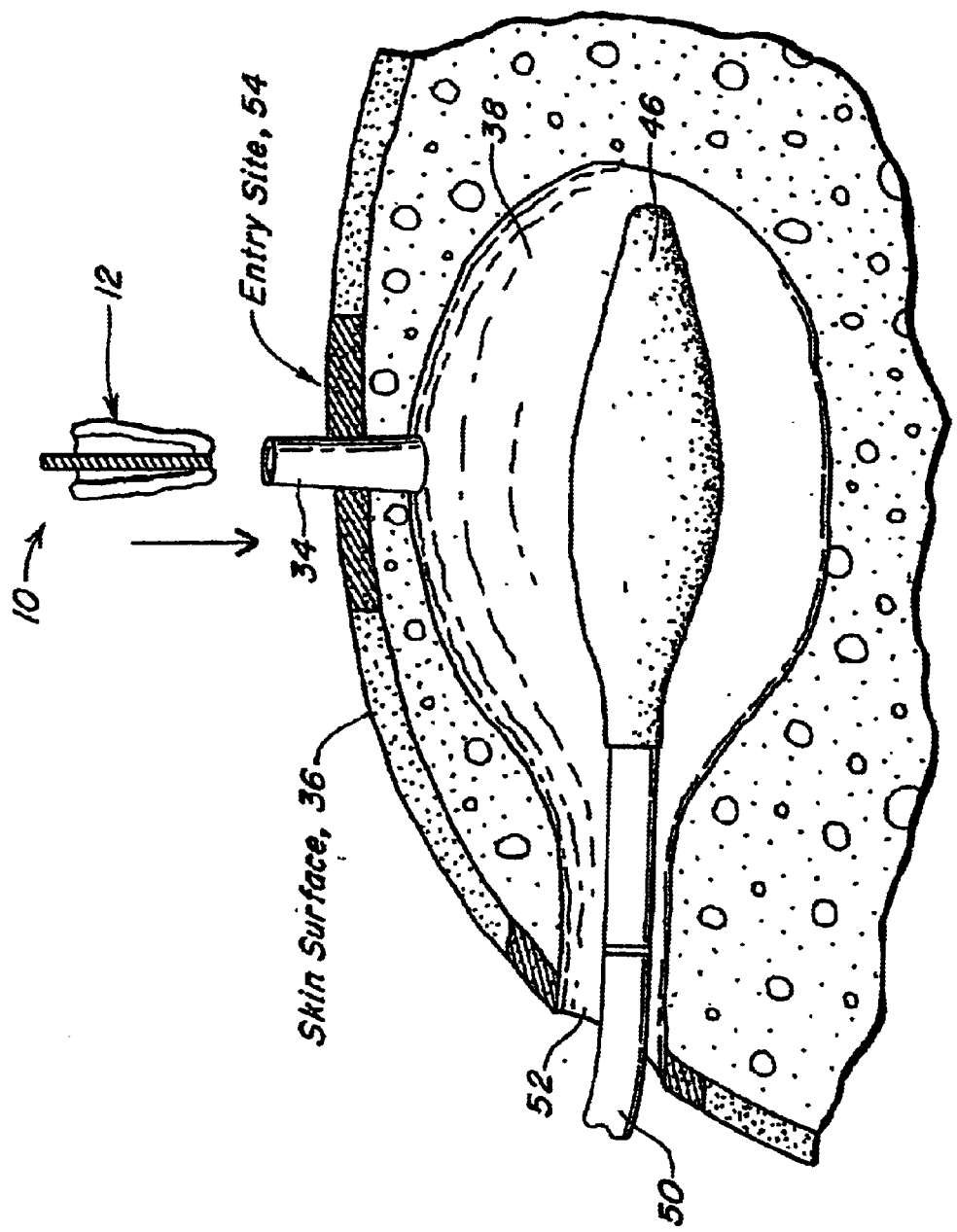
FIG. 5A illustrates a brachytherapy device disposed within a surgical extraction site, and a spacing apparatus according to the present invention prior to insertion into the surgical extraction site.
Figure 5D:
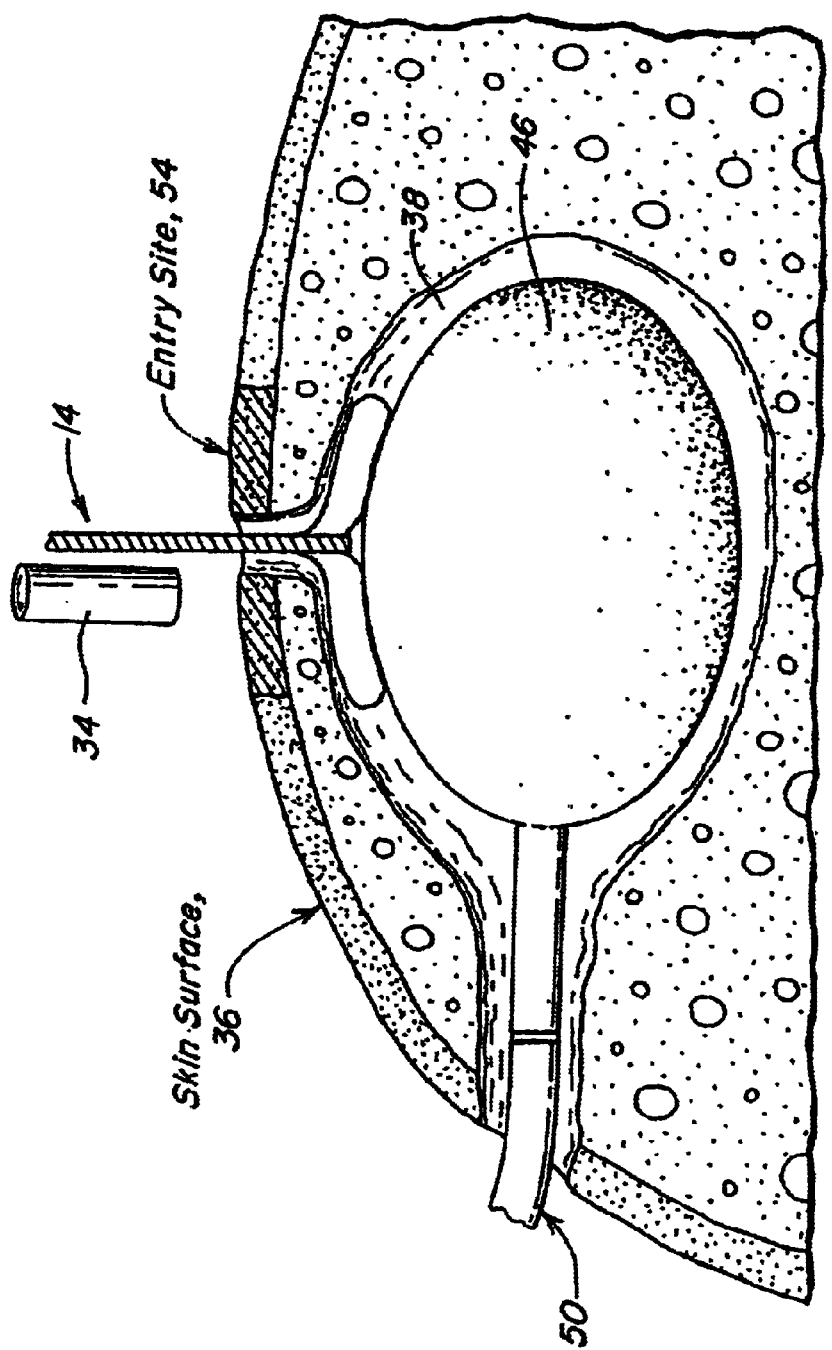
FIG. 5D illustrates a brachytherapy device positioned at a distance apart from tissue disposed adjacent a surgical extraction site by the spacing apparatus of FIG. 5A, which is shown extended into an open position.

Once spacing apparatus 10 is fully inserted into resection cavity 38, spacing element 12 is moved to its open position, as shown in FIG. 5C. Spacing apparatus 10 can then be retracted, or can be pushed against an outer surface of the resection cavity 38 upon inflation of the balloon member 46 of the brachytherapy device 50. Introducer sheath 34 can optionally be removed, leaving spacing apparatus 10 abutting an outer surface of resection cavity 38, as shown in FIG. 5D, and maintaining the brachytherapy device at the desired spacing apart from skin 36.

It will be understood that the foregoing is only illustrative of the principles of the invention, and that various modifications can be made by those skilled in the art without departing from the scope and spirit of the invention, including, but not limited to, combinations of elements from different embodiments found herein. All references cited herein are expressly incorporated by reference in their entirety.

What is claimed is:

1. A brachytherapy device, comprising:
    an insertion member having a proximal end and a distal end;
    an expandable surface member disposed on the distal end of the insertion member and effective to receive a radiation source for treating target tissue surrounding a surgical extraction site;
    a spacing element disposed adjacent to and not surrounding the expandable surface member, the spacing element having a predeterminable height and being adapted to position the expandable surface member at a distance apart from tissue surrounding the surgical extraction site, the distance being equal to the height of the spacing element.

2. The brachytherapy device of claim 1, wherein the spacing element is movable between a closed position in which the spacing element is disposed adjacent the insertion member, and an open position in which the spacing element extends outward from the insertion member.

3. The brachytherapy device of claim 2, wherein the spacing element comprises a second expandable balloon member.

4. The brachytherapy device of claim 3, wherein the spacing element is expanded in the open position, and is deflated in the closed position, and wherein the spacing element has a predetermined shape in the open position such that, when inflated, the spacing element is effective to position the brachytherapy device at a predeterminable distance apart from tissue surrounding the surgical extraction site.

5. The brachytherapy device of claim 4, wherein the predetermined shape of the spacing element is substantially disk-shaped.

6. The brachytherapy device of claim 2, wherein the expandable surface member, upon inflation, is effective to move the spacing element to the open position.

7. The brachytherapy device of claim 6, wherein the spacing element in the open position is effective to position the expandable surface member at a distance apart from tissue surrounding the surgical extraction site.

8. A brachytherapy positioning system, comprising:
    a brachytherapy device for treating target tissue surrounding a surgical extraction site;
    a spacing apparatus adjacent to and not surrounding the first expandable surface member, comprising a spacing element having a predeterminable height and being adapted to position the brachytherapy device at a distance apart from tissue surrounding the surgical extraction site, the distance being equal to the height of the spacing element.

9. The brachytherapy positioning system of claim 8, wherein the spacing element is effective to form a radio-opaque barrier between the brachytherapy device and the tissue surrounding the surgical extraction site.

10. The brachytherapy positioning system of claim 8, further comprising an insertion member having a proximal end and a distal end, the spacing element being disposed on the distal end of the insertion member.

11. The brachytherapy positioning system of claim 10, wherein the spacing element is formed integrally with the distal end of the insertion member.

12. The brachytherapy positioning system of claim 11, wherein the spacing element is formed of a shape memory material, the spacing member having a first shape in a closed position for inserting the spacing element into a surgical extraction site, and a second shape in an open position, the spacing member being deployable into the open position in the surgical extraction site for positioning the brachytherapy device at a predetermined distance apart from sensitive tissue.

13. The brachytherapy system of claim 10, wherein the spacing element is movable between a closed position in which the spacing element is disposed adjacent the insertion member, and an open position in which the spacing element extends outward from the insertion member.

14. The brachytherapy positioning system of claim 13, wherein the spacing element in the open position is effective to position the brachytherapy device at a distance apart from tissue surrounding the surgical extraction site.

15. The brachytherapy positioning system of claim 14, wherein the spacing element has a three-dimensional shape in the open position, and a substantially folded shape in the closed position, and wherein the spacing element is formed of a shape memory material and is biased to the open position.

16. The brachytherapy positioning system of claim 15, wherein the spacing element is disk-shaped in the open position.

17. The brachytherapy positioning system of claim 11, wherein the spacing element comprises an expandable balloon member disposed on a portion of the insertion member.

18. The brachytherapy positioning system of claim 17, wherein the expandable balloon member is inflated in the open position, and is deflated in the closed position, and wherein the expandable balloon member has a predetermined shape in the open position such that, when inflated, the balloon member is effective to position the brachytherapy device at a predeterminable distance apart from tissue surrounding the surgical extraction site.

19. The brachytherapy positioning system of claim 18, wherein the predetermined shape of the expandable balloon member is substantially disk-shaped.

* * * * *